United States Patent
Cacciola et al.

(10) Patent No.: US 7,781,434 B2
(45) Date of Patent: Aug. 24, 2010

(54) METABOTROPIC GLUTAMATE RECEPTOR ISOXAZOLE LIGANDS AND THEIR USE AS POTENTIATORS—286

(75) Inventors: Joseph Cacciola, Wilmington, DE (US); James Empfield, Wilmington, DE (US); James Folmer, Wilmington, DE (US); Angela M Hunter, Wilmington, DE (US); Scott Throner, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/575,891

(22) Filed: Oct. 8, 2009

(65) Prior Publication Data

US 2010/0022545 A1 Jan. 28, 2010

Related U.S. Application Data

(63) Continuation of application No. 12/477,347, filed on Jun. 3, 2009.

(60) Provisional application No. 61/059,485, filed on Jun. 6, 2008.

(51) Int. Cl.
*A61K 31/5377* (2006.01)
*C07D 413/14* (2006.01)

(52) U.S. Cl. .................. 514/235.2; 544/140
(58) Field of Classification Search .......... 514/235.2; 544/140
See application file for complete search history.

(56) References Cited

U.S. PATENT DOCUMENTS

| 2009/0111830 A1* | 4/2009 | Wagenen et al. ....... 514/253.09 |
| 2009/0149505 A1* | 6/2009 | Empfield et al. ............ 514/339 |
| 2009/0306158 A1* | 12/2009 | Cacciola et al. ............ 514/378 |

FOREIGN PATENT DOCUMENTS

| EP | 1726585 | * | 11/2006 |
| WO | WO 2006020879 | * | 2/2006 |
| WO | WO 2007021309 | * | 2/2007 |
| WO | WO 2007095024 | * | 8/2007 |

* cited by examiner

*Primary Examiner*—Rebecca L Anderson
(74) *Attorney, Agent, or Firm*—Kenneth F. Mitchell

(57) ABSTRACT

Compounds in accord with Formula I:

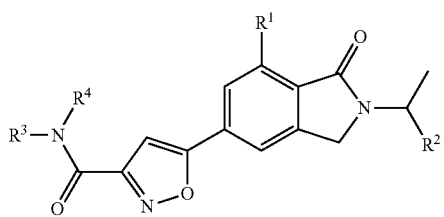

wherein $R^1$, $R^2$, $R^3$ and $R^4$ are as defined in the specification, pharmaceutically acceptable salts, methods of making, pharmaceutical compositions containing and methods for using the same.

7 Claims, No Drawings

METABOTROPIC GLUTAMATE RECEPTOR ISOXAZOLE LIGANDS AND THEIR USE AS POTENTIATORS—286

This is a Continuation of U.S. application Ser. No. 12/477,347 filed Jun. 3, 2009, which claims the benefit under 35 U.S.C. §119(e) of U.S. Provisional Application No. 61/059,485, filed Jun. 6, 2008.

FIELD OF THE INVENTION

The present invention relates to isoxazole derivatives that function as potentiators of glutamate receptors, methods for their preparation, pharmaceutical compositions containing them and their use in therapy.

BACKGROUND

The metabotropic glutamate receptors (mGluR) constitute a family of GTP-binding-protein (G-protein) coupled receptors that are activated by glutamate, and have important roles in synaptic activity in the central nervous system, including neural plasticity, neural development and neurodegeneration.

Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels (Schoepp et al., 1993, Trends Pharmacol. Sci., 14:13; Schoepp, 1994, Neurochem. Int., 24:439; Pin et al., 1995, Neuropharmacology 34:1; Bordi & Ugolini, 1999, Prog. Neurobiol. 59:55).

Eight mGluR subtypes have been identified, which are divided into three groups based upon primary sequence similarity, signal transduction linkages, and pharmacological profile. Group-I includes mGluR1 and mGluR5, which activate phospholipase C and the generation of an intracellular calcium signal. The Group-II (mGluR2 and mGluR3) and Group-III (mGluR4, mGluR6, mGluR7, and mGluR8) mGluRs mediate an inhibition of adenylyl cyclase activity and cyclic AMP levels. For a review, see Pin et al., 1999, Eur. J. Pharmacol., 375:277-294.

Activity of mGluR family receptors are implicated in a number of normal processes in the mammalian CNS, and are important targets for compounds for the treatment of a variety of neurological and psychiatric disorders. Activation of mGluRs is required for induction of hippocampal long-term potentiation and cerebellar long-term depression (Bashir et al., 1993, Nature, 363:347; Bortolotto et al., 1994, Nature, 368:740; Aiba et al., 1994, Cell, 79:365 Aiba et al., 1994, Cell, 79:377). A role for mGluR activation in nociception and analgesia also has been demonstrated (Meller et al., 1993, Neuroreport, 4: 879; Bordi & Ugolini, 1999, Brain Res., 871:223). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex (Nakanishi, 1994, Neuron, 13:1031; Pin et al., 1995, Neuropharmacology, supra; Knopfel et al., 1995, J. Med. Chem., 38:1417).

Recent advances in the elucidation of the neurophysiological roles of mGluRs have established these receptors as promising drug targets in the therapy of acute and chronic neurological and psychiatric disorders and chronic and acute pain disorders. Because of the physiological and pathophysiological significance of the mGluRs, there is a need for new drugs and compounds that can modulate mGluR function.

DESCRIPTION OF THE INVENTION

We have identified a class of compounds that modulate mGluR function. In one form the invention provides a compound of Formula I, or a pharmaceutically acceptable salt, hydrate, solvate, or enantiomer thereof.

Thus, in one embodiment, the present invention provides a composition of matter comprising a compound in accord with Formula I:

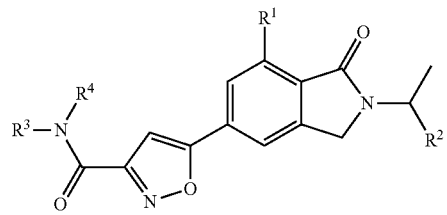

I wherein:

$R^1$ is selected from $C_{1-3}$alkyl or halogen;

$R^2$ is selected from $C_{1-3}$alkyl, $C_{1-3}$haloalkyl or $C_{3-6}$cycloalkyl;

$R^3$ and $R^4$ at each occurrence are independently selected from hydrogen, $C_{1-3}$alkyl, $C_{1-3}$hydroxyalkyl, $C_{3-6}$carbocyclyl, heterocyclyl or heteroaryl, or $R^3$ and $R^4$ in combination with the nitrogen to which they are attached form a cyclic moiety selected from morpholino, pyrrolidinyl or piperazinyl.

In a particular aspect, this embodiment provides compounds wherein $R^2$ is methyl, of Formula I:

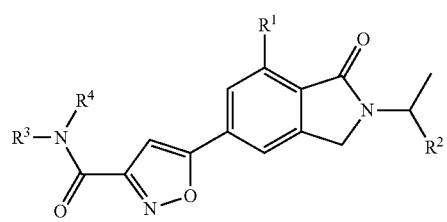

I or compounds wherein $R^2$ is trifluoromethyl or cyclopropyl of Formula II, substantially free of other enantiomers:

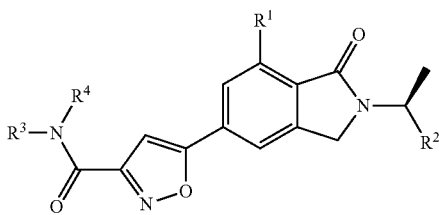

wherein:

R¹ is selected from methyl or chloro;

R³ and R⁴ at each occurrence are independently selected from hydrogen, methyl, isopropyl, 2-hydroxyethyl, cyclopentyl, cyclohexyl, piperidinyl or pyrazolyl, or R³ and R⁴ in combination with the nitrogen to which they are attached form a cyclic moiety selected from morpholino, pyrrolidinyl or piperazinyl.

In another particular aspect, this embodiment provides compounds in accord with Formula I wherein:

R¹ and R² are methyl;

R³ and R⁴ in combination with the nitrogen to which they are attached form a cyclic moiety selected from morpholino or pyrrolidinyl.

In yet another particular aspect, this embodiment provides compounds in accord with Formula II, substantially free of other enantiomers, wherein:

R¹ is chloro;

R² is trifluoromethyl or cyclopropyl;

R³ and R⁴ at each occurrence are independently selected from hydrogen, methyl or isopropyl.

In another aspect, this embodiment provides compounds in accord with Formula II, substantially free of other enantiomers wherein:

R¹ is selected from methyl or chloro;

R² is selected from trifluoromethyl or cyclopropyl;

R³ is hydrogen or methyl, and

R⁴ is selected from hydrogen, methyl, cyclopentyl or cyclohexyl.

In particular this embodiment provides the compounds described in the Examples herein as follows:

5-(7-chloro-2-((S)-1-cyclopropylethyl)-1-oxo-2,3-dihydro-1H-isoindolin-5-yl)-N-methylisoxazole-3-carboxamide;
5-(7-chloro-2-((S)-1-cyclopropylethyl)-1-oxo-2,3-dihydro-1H-isoindolin-5-yl)-N,N-dimethylisoxazole-3-carboxamide;
5-[7-Chloro-2-((S)-1-cyclopropyl-ethyl)-1-oxo-2,3-dihydro-1H-isoindol-5-yl]-isoxazole-3-carboxylic acid amide;
5-[2-((S)-1-Cyclopropyl-ethyl)-7-methyl-1-oxo-2,3-dihydro-1H-isoindol-5-yl]-isoxazole-3-carboxylic acid amide;
5-(2-Isopropyl-7-methyl-1-oxo-2,3-dihydro-1H-isoindol-5-yl)-isoxazole-3-carboxylic acid dimethylamide;
5-[2-((S)-1-Cyclopropyl-ethyl)-7-methyl-1-oxo-2,3-dihydro-1H-isoindol-5-yl]-isoxazole-3-carboxylic acid methylamide;
5-[7-Chloro-2-((S)-1-cyclopropyl-ethyl)-1-oxo-2,3-dihydro-1H-isoindol-5-yl]-isoxazole-3-carboxylic acid amide;
5-[2-((S)-1-Cyclopropyl-ethyl)-7-methyl-1-oxo-2,3-dihydro-1H-isoindol-5-yl]-isoxazole-3-carboxylic acid dimethylamide;
7-Chloro-2-isopropyl-5-[3-(pyrrolidine-1-carbonyl)-isoxazol-5-yl]-2,3-dihydro-isoindol-1-one;
5-(7-Chloro-2-isopropyl-1-oxo-2,3-dihydro-1H-isoindol-5-yl)-isoxazole-3-carboxylic acid (2-hydroxy-ethyl)-methyl-amide;
5-[7-Methyl-1-oxo-2-((S)-2,2,2-trifluoro-1-methyl-ethyl)-2,3-dihydro-1H-isoindol-5-yl]-isoxazole-3-carboxylic acid dimethylamide;
5-[2-((S)-1-Cyclopropyl-ethyl)-7-methyl-1-oxo-2,3-dihydro-1H-isoindol-5-yl]-isoxazole-3-carboxylic acid isopropyl-methyl-amide;
5-[2-((S)-1-Cyclopropyl-ethyl)-7-methyl-1-oxo-2,3-dihydro-1H-isoindol-5-yl]-isoxazole-3-carboxylic acid (2-hydroxy-ethyl)-methyl-amide;
5-(7-Chloro-2-isopropyl-1-oxo-2,3-dihydro-1H-isoindol-5-yl)-isoxazole-3-carboxylic acid cyclopentylamide;
7-Chloro-2-isopropyl-5-[3-(morpholine-4-carbonyl)-isoxazol-5-yl]-2,3-dihydro-isoindol-1-one;
2-((S)-1-Cyclopropyl-ethyl)-7-methyl-5-[3-(piperazine-1-carbonyl)-isoxazol-5-yl]-2,3-dihydro-isoindol-1-one;
5-[7-Chloro-1-oxo-2-((S)-2,2,2-trifluoro-1-methyl-ethyl)-2,3-dihydro-1H-isoindol-5-yl]-isoxazole-3-carboxylic acid dimethylamide;
5-[7-Chloro-2-((S)-1-cyclopropyl-ethyl)-1-oxo-2,3-dihydro-1H-isoindol-5-yl]-isoxazole-3-carboxylic acid isopropyl-methyl-amide;
5-[7-Chloro-2-((S)-1-cyclopropyl-ethyl)-1-oxo-2,3-dihydro-1H-isoindol-5-yl]-isoxazole-3-carboxylic acid (2-hydroxy-ethyl)-methyl-amide;
7-Chloro-2-((S)-1-cyclopropyl-ethyl)-5-[3-(morpholine-4-carbonyl)-isoxazol-5-yl]-2,3-dihydro-isoindol-1-one, and
7-Chloro-5-[3-(morpholine-4-carbonyl)-isoxazol-5-yl]-2-((S)-2,2,2-trifluoro-1-methyl-ethyl)-2,3-dihydro-isoindol-1-one.

Also provided are processes for making compounds of Formula I or Formula II.

Further provided are pharmaceutical compositions comprising a compound according to Formula I or Formula II together with a pharmaceutically acceptable carrier or excipient.

In another embodiment, a method for the treatment or prevention of neurological and psychiatric disorders associated with glutamate dysfunction in an animal in need of such treatment is provided. The method comprises a step of administering to the animal a therapeutically effective amount of a compound of Formula I or Formula II, or a pharmaceutical composition comprising such an amount.

The invention also provides for the use of a compound according to Formula I or II, or a pharmaceutically acceptable salt or solvate thereof, in the manufacture of a medicament for the treatment of conditions mentioned herein.

Further, the invention provides a compound of Formula I or II, or a pharmaceutically acceptable salt or solvate thereof, for use in therapy.

Compounds described herein exhibit activity as modulators of metabotropic glutamate receptors and more particularly exhibit activity as potentiators of the mGluR2 receptor. It is contemplated that the compounds will be useful in therapy as pharmaceuticals, in particular for the treatment of neurological and psychiatric disorders associated with glutamate dysfunction.

DEFINITIONS

Unless described otherwise within this specification, the nomenclature used in this specification generally follows the examples and rules stated in *Nomenclature of Organic Chemistry*, Sections A, B, C, D, E, F and H, Pergamon Press, Oxford, 1979, which is incorporated by references herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

The term "$C_{1-3}$alkyl" as used herein means a straight-, branched-chain or cyclic hydrocarbon radical having from one to three carbon atoms, and includes methyl, ethyl, propyl, isopropyl, and cyclopropyl.

The term "$C_{1-3}$haloalkoxyl" as used herein means a straight- or branched-chain alkoxy radical having from one to three carbon atoms and at least one halo substituent and includes fluoromethoxyl, trifluoromethoxyl, fluoroethoxyl, trifluoropropyloxyl, fluoroisopropyloxy and the like.

The term "halo" as used herein means halogen and includes fluoro, chloro, bromo, iodo, in both radioactive and non-radioactive forms.

The symbol Δ when used herein means heating or the application of heat.

The term "pharmaceutically acceptable salt" means either an acidic addition salt or a basic addition salt that is compatible with the administration to patients.

A "pharmaceutically acceptable acidic addition salt" is any non-toxic organic or inorganic acidic addition salt of a compound represented by Formula I. Illustrative inorganic acids that form suitable salts include hydrochloric, hydrobromic, sulfuric and phosphoric acid and acid metal salts such as sodium monohydrogen orthophosphate and potassium hydrogen sulfate. Illustrative organic acids that form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Where chemically feasible, mono- or di-acid salts can be formed and such salts can exist in either a hydrated solvated or substantially anhydrous form. In general, the acidic addition salts of these compounds are more soluble in water and various hydrophilic organic solvents and generally demonstrate higher melting points in comparison to their free base forms. Other salts, e.g. oxalates, may be used, for example in the isolation of compounds of Formula I for laboratory use or for subsequent conversion to a pharmaceutically acceptable acidic addition salt.

"Solvate" means a compound of Formula I or the pharmaceutically acceptable salt of a compound of Formula I wherein molecules of a suitable solvent are incorporated in a crystal lattice. A suitable solvent is physiologically tolerable at the dosage administered as the solvate. Examples of suitable solvents are ethanol, water and the like. When water is the solvent, the molecule is referred to as a hydrate.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound that is effective in treating the named disorder or condition.

The term "pharmaceutically acceptable carrier" means a non-toxic solvent, dispersant, excipient, adjuvant or other material that is mixed with the active ingredient in order to permit the formation of a pharmaceutical composition, i.e., a dosage form capable of administration to the patient. One example of such a carrier is a pharmaceutically acceptable oil typically used for parenteral administration.

A pharmaceutically acceptable salt, hydrate, solvate, or combination thereof of each of the mentioned embodiments is contemplated to be within the scope of the invention.

The optically active forms of the compound of the invention may be prepared, for example, by chiral chromatographic separation of a racemate, by synthesis from optically active starting materials or by asymmetric synthesis.

It will also be understood by those of skill in the art that certain compounds of the present invention may exist in a solvated, for example hydrated, as well as an unsolvated form. It will further be understood that the present invention encompasses all such solvated forms of the compounds of Formula I or Formula II.

Within the scope of the invention are also salts of the compounds of Formula I or Formula II. Generally, pharmaceutically acceptable salts of compounds of the present invention are obtained using standard procedures well known in the art.

In one embodiment of the present invention, a compound of Formula I or Formula II may be converted to a pharmaceutically acceptable salt or solvate thereof, such as a hydrochloride, hydrobromide, phosphate, acetate, fumarate, maleate, tartrate, citrate, methanesulphonate or p-toluenesulphonate.

Processes for Preparing Compounds

Compounds according to Formula I may generally be prepared by the synthetic processes illustrated herein. The choice of particular structural features and/or substituents may influence the selection of one process over another and may influence the conditions under which the process is carried out.

Within these general guidelines, processes described herein can be used to prepare exemplary compounds of this invention. Unless indicated otherwise, the variables in the described schemes and processes have the same definitions as those given for Formulae I and II herein. Also for avoidance of doubt, in general when Formula I is referred to it will be understood to encompass compounds of Formula II.

A person of ordinary skill in the art thus will appreciate that other compounds in accord with Formula I may be made by variations and additions adapting one or more of the processes disclosed herein.

The invention is further illustrated by way of the examples herein, which describe several embodiments of the invention. The synthetic scheme and the synthetic procedures provided for Examples 1 and 2 are provided by way of illustration and are not to be construed as limiting the invention. It will be clear to those skilled in the art that compounds other than those illustrated may be readily prepared by processes analogous to those described.

General Methods

Starting materials are commercially available or are described in the literature.

$^1$H and $^{13}$C NMR spectra were recorded either on Bruker 300, Bruker DPX400 or Varian +400 spectrometers operating at 300, 400 and 500 MHz for $^1$H NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, br s: broad singlet, d: doublet, t: triplet, q: quartet, m: multiplet).

Analytical in-line liquid chromatography separations followed by mass spectra detections, were recorded on a Waters LCMS consisting of an Alliance 2795 (LC) and a ZQ single quadrapole mass spectrometer. The mass spectrometer was equipped with an electrospray ion source operated in a positive and/or negative ion mode. The ion spray voltage was ±3 kV and the mass spectrometer was scanned from m/z 100-700 at a scan time of 0.8 s. To the column, X-Terra MS, Waters, C8, 2.1×50 mm, 3.5 mm, was applied a linear gradient from 5% to 100% acetonitrile in 10 mM ammonium acetate (aq.), or in 0.05 to 0.1% formic acid (aq.).

Purification of products was done using Silicycle SilicaFlash Catridges (cat # FLH-R10030B) on an ISCO automated flash chromatography system, or by flash chromatography in silica-filled glass columns.

Microwave heating was performed in an Emrys Optimizer Single-mode microwave cavity producing continuous irradiation at 2450 MHz (Personal Chemistry AB, Uppsala, Sweden).

LC-MS HPLC Conditions:

Method A: Column: Waters Acquity UPLC BEH-C18, 1.7 µm, 2.1 mm ID×50 mm Flow: 1.0 mL/min. Gradient: 95% A to 95% B over 0.9 minutes hold 0.3 minutes ramp down to 95% A over 0.1 minute following a standard linear gradient. Where A=2% acetonitrile in water with 0.1% formic acid and B=2% water in acetonitrile with 0.05% formic acid. UV-DAD 210-400 nm.

Method B: Column: Agilent Zorbax SB-C8, 5 µm, 2.1 mm ID×50 mm Flow: 1.4 mL/min, Gradient: 95% A to 90% B over 3 minutes hold 1 minute ramp down to 95% A over 1 minute and hold 1 minute following a standard linear gradient. Where A=2% acetonitrile in water with 0.1% formic acid and B=2% water in acetonitrile with 0.05% formic acid. UV-DAD 210-400 nm.

The instruments, methods and conditions described herein are provided by way of illustration and are not to be construed as limiting the invention. Those of skill in the art will appreciate that other instruments and methods may be used to make the measurements or achieve the separations described.

Synthetic Processes:

Scheme 1 illustrates a representative synthesis of a 6-substituted 4-bromo-2-bromomethyl-benzoic acid methyl ester from commercially available precursors wherein the respective reaction steps comprise as follows: (a) NaNO₂, aq. HCl; (b) NaCN, CuCN and HCl; (c) NaOH; (d) nitrososulphuric acid; (e) MeI and K₂CO₃, and (f) NBS and (PhCO₂)₂. Briefly, a 4-bromo-aniline may be diazotized under Sandmeyer reaction conditions, followed by conversion to the nitrile using sodium cyanide and copper cyanide. The nitrile may then be hydrolyzed to an amide by basic hydrolysis. The amide can then be hydrolyzed with nitrososulphuric acid to provide a benzoic acid, which may be converted to a methyl ester under standard conditions. The benzylic methyl group may be monobrominated with N-bromosuccinimide using benzoyl peroxide as a radical initiator to yield a desired 6-substituted 4-bromo-2-bromomethyl-benzoic acid methyl ester.

Scheme 1:

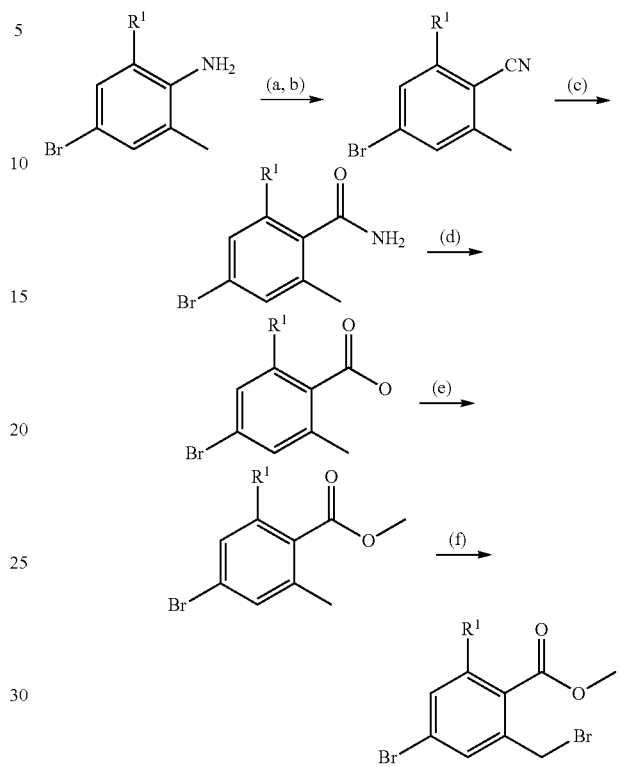

A 6-substituted 4-bromo-2-bromomethyl-benzoic acid methyl ester may be cyclized to an isoindoline with an amine, or a chiral amine if a chiral compound is desired, (g) $CH_3CHR^2NH_2$, $K_2CO_3$, $B(OH)_3$, as shown in Scheme 2.

Scheme 2:

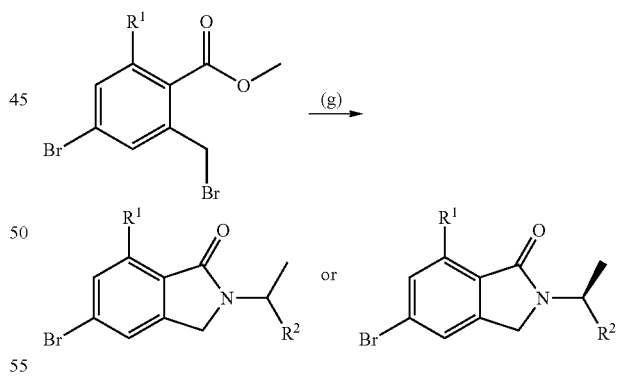

A compound of Formula I (or Formula II) may be prepared from an isoindoline by a series of reactions steps as shown in Scheme 3, as follows: (h) $Pd(BnCN)_2Cl_2$, TMS-≡, $Cu(OAc)_2$, $PPh_3$ in diisopropyl amine under gentle heating for 2 hrs; (i) KOH, EtOH/H₂O, 1 Hr at RT; (j) ethyl 2-chloro-2-(hydroxyimino)acetate, KHCO₃, EA/H₂O, 16 Hr at RT and (k) NaOH, MeOH/H₂O, 1 Hr at RT, followed by (l) IBCF, NMM, $R^3R^4NH$ in THF at −20° C. Briefly, a 4-bromo-isoindolone may be reacted under Sonagashira conditions with a protected acetylene. Deprotection of the acetylene with base, followed by reaction with ethyl 2-chloro-2-(hydroxyimino) acetate will generate an isoxazole ester. Finally, hydrolysis of the ester to the acid and amidation using isobutylchloroformate, N-methyl morpholine and an appropriate amine, will generate a desired amide. Alternatively, an amide can be generated via an isoxazole ester directly by step (m) by reaction with an amine, $R^3R^4NH$ in ethanol, and heating.

A solution of ethyl 5-(7-chloro-2-((S)-1-cyclopropylethyl)-1-oxoisoindolin-5-yl)isoxazole-3-carboxylate (29.59 g, 78.94 mmol) in ethanol (500 mL) was treated with a 33% solution of ethanolic dimethylamine (352 mL, 1973.6 mmol).

Scheme 3:

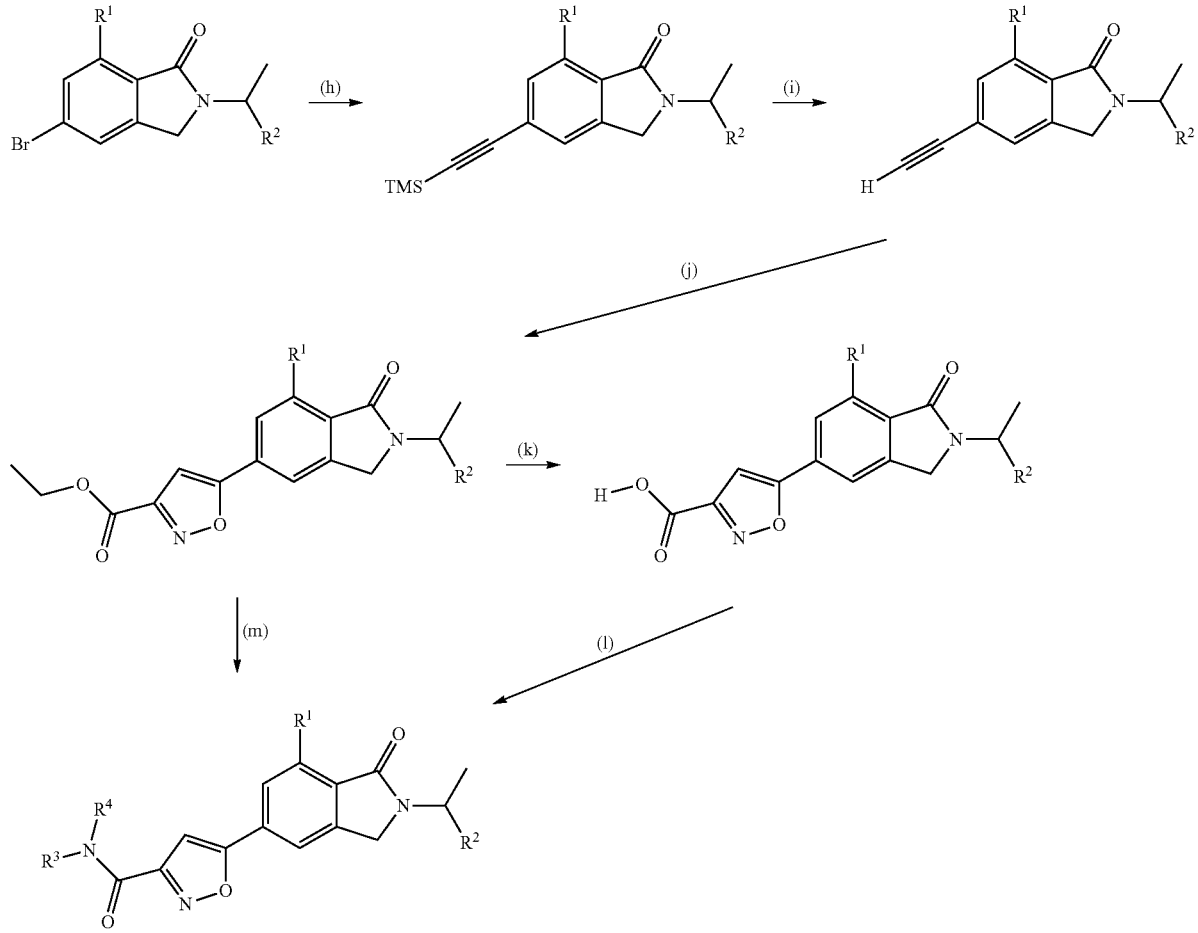

EXAMPLES

Example 1

5-(7-chloro-2-((S)-1-cyclopropylethyl)-1-oxo-2,3-dihydro-1H-isoindolin-5-yl)-N,N-dimethylisoxazole-3-carboxamide

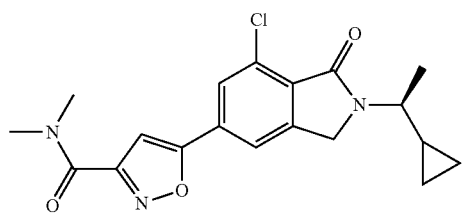

The resulting light-green solution was gently warmed for approximately 3 hours, with sufficient heating to maintain a clear solution (approximately 50° C.). The reaction was cooled to room temperature and the volatiles removed under reduced pressure. The material was purified by flash chromatography on silica gel eluting with a gradient of 0 to 50% ethyl acetate in methylene chloride to afford the desired compound. The isolated product was then subjected to an additional purification step by crystallization in ethanol. The 5-(7-chloro-2-((S)-1-cyclopropylethyl)-1-oxoisoindolin-5-yl)-N,N-dimethylisoxazole-3-carboxamide (34.88 g, 93.30 mmol) was taken up in approximately 350 mL of ethanol and warmed to 70-80° C. until all of the product dissolved. The solution was quickly filtered through a medium glass frit, warmed back up to 70-80° C. and filtered through a paper filter (Whatman #1). The filtrate was heated again to 70-80° C. to assure a clear solution and allowed to slowly cool to room temperature (the final volume of solvent was 450 mL). After sitting overnight, fine crystals of the title product formed. The mixture was cooled in a refrigerator for an additional 2 hours. The crystals were isolated by filtration, washed with cold ethanol and dried under high vacuum at room temperature to afford white, small needle-like crystals (27.21 g, 78%). Mp 143.5° C. ¹H NMR (300 MHz, DMSO-d₆) δ ppm 0.21-0.32 (m, 1H) 0.35-0.50 (m, 2H) 0.53-0.67 (m, 1H) 1.16 (dd, 1H) 1.30 (d, 3H) 3.06 (s, 3H) 3.14 (s, 3H), 3.59 (dd, 1H) 4.62 (s, 2H) 7.50 (s, 1H) 8.06 (s, 1H) 8.11 (s, 1H). MS ESI, m/z=374 (M+H). HPLC Method B: 0.70 min.

Intermediate compounds were prepared as follows:

a) Ethyl 5-(7-chloro-2-((S)-1-cyclopropylethyl)-1-oxoisoindolin-5-yl)isoxazole-3-carboxylate 7-chloro-2-((S)-1-cyclopropylethyl)-5-ethynylisoindolin-1-one (28.66 g, 110.35 mmol) and potassium hydrogen carbonate (110.0 g, 1103.45 mmol) were dissolved in a solution consisting of 1200 mL of ethyl acetate and 400 mL of water. To this solution was added ethyl 2-chloro-2-(hydroxyimino)acetate (66.9 g, 441.38 mmol). The ethyl 2-chloro-2-(hydroxyimino)acetate was added at room temperature as a solution in 160 mL of ethyl acetate via syringe pump at a rate of 5 mL/Hr. Following the addition of the ethyl 2-chloro-2 (hydroxyimino)acetate, the reaction was allowed to continue stirring at room temperature for an additional 12 hours. The ethyl acetate layer was extracted in a separatory funnel, dried over magnesium sulfate, filtered and concentrated under reduced pressure. The material was purified by flash chromatography on silica gel eluting with a gradient of 0 to 25% ethyl acetate in hexane to afford the title compound as a white solid (17.05 g, 41.2%). ¹H NMR (300 MHz, CDCl₃) δ ppm 0.36-0.53 (m, 3H) 0.63-0.73 (m, 1H) 0.98-1.12 (m, 1H) 1.38 (d, 3H) 1.47 (t, 3H) 3.80 (dq, 1H) 4.43-4.65 (m, 4H) 7.05 (s, 1H) 7.83 (s, 2H). MS ESI, m/z=375 (M+H). HPLC Method B: 0.82 min b) 7-chloro-2-((S)-1-cyclopropylethyl)-5-ethynyl-isoindolin-1-one 7-chloro-2-((S)-1-cyclopropylethyl)-5-(2-(trimethylsilyl)ethynyl)isoindolin-1-one (40.88 g, 123.17 mmol) was dissolved in 250 mL of ethanol and stirred at room temperature. To the reaction mixture was added a solution of potassium hydroxide (0.10 g, 1.85 mmol) in 20 mL of water. The reaction immediately turned black and was allowed to continue stirring for 90 minutes at room temperature. The volatiles were removed under reduced pressure and the product purified by flash chromatography on silica gel eluting with a gradient of 0 to 40% ethyl acetate in hexane. This afforded the desired product as a light tan solid (20.75 g, 69.7%). ¹H NMR (300 MHz, CDCl₃) δ ppm 0.34-0.50 (m, 3H) 0.58-0.69 (m, 0.93-1.07 (m, 1H) 1.34 (d, 3H) 3.22 (s, 1H) 3.76 (dq, 1H) 4.31-4.54 (m, 2H) 7.45 (s, 1H) 7.51 (s, 1H). MS ESI m/z=260 (M+H). HPLC Method B: 0.80 min.

c) 7-chloro-2-((S)-1-cyclopropylethyl)-5-(2-(trimethylsilyl)ethynyl)isoindolin-1-one 5-bromo-7-chloro-2-((S)-1-cyclopropylethyl)isoindolin-1-one (5.0 g, 15.89 mmol) was placed in a 3-neck flask, fitted with an internal thermocouple and dissolved in 150 mL of degassed diisopropyl amine. To this solution was added copper (II) acetate (0.14 g, 0.79 mmol), triphenylphosphine (0.417 g, 1.59 mmol) and bis(benzonitrile)dichloropalladium (II) (0.30 g, 0.79 mmol). Finally, ethynyltrimethylsilane (4.84 mL, 34.96 mmol) was added dropwise over a 20-min period. After the addition of the silane was complete, the reaction mixture was heated to and held at 65° C. until starting material was consumed (as monitored by LC/MS). The reaction was allowed to cool to room temperature and the volatiles were removed under reduced pressure. The material was then filtered through a glass frit and the remaining solids in the frit were rinsed with diethyl ether. The volatiles were again removed under reduced pressure and the concentrated residue was purified by flash chromatography on silica gel eluting with 0 to 40% ethyl acetate in hexane. This afforded the title compound as a tan solid (4.90 g, 93%). ¹H NMR (300 MHz, CDCl₃) δ ppm 0.18-0.22 (m, 9H) 0.29-0.43 (m, 3H) 0.53-0.62 (m, 1H) 0.88-1.01 (m, 1H) 1.27 (d, 3H) 3.69 (dq, 1H) 4.33 (q, 2 H) 7.35 (d, 1H) 7.42 (s, 1H). MS ESI, m/z=332 (M+H). HPLC Method A: 1.05 min.

Example 2

5-(7-chloro-2-((S)-1-cyclopropylethyl)-1-oxo-2,3-dihydro-1H-isoindolin-5-yl)-N-methylisoxazole-3-carboxamide

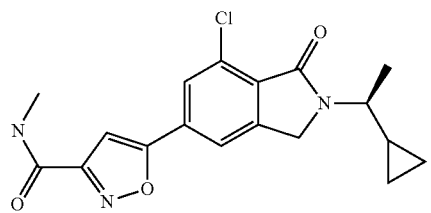

Ethyl 5-(7-chloro-2-((S)-1-cyclopropylethyl)-1-oxoisoindolin-5-yl)isoxazole-3-carboxylate (4.00 g, 10.67 mmol) was placed into a 200 mL pressure vessel followed by the addition of ethanol (20 mL) and a 33% solution of ethanolic methylamine (57.2 mL, 320.16 mmol). The solution was warmed to and held at 55° C. for 10 minutes and then cooled to room temperature. A precipitate formed, was collected by filtration and dried overnight in a 40° C. vacuum oven. Residual ethanol was removed from the isolated product by dissolving the solids in a minimal amount of methylene chloride followed by removal of the volatiles under reduced pressure to afford the title compound (3.46 g, 90%), Mp 212.3° C. ¹H NMR (300 MHz, CDCl₃) δ ppm 0.28-0.46 (m, 3H) 0.54-0.64 (m, 1H) 0.90-1.02 (m, 1H) 1.30 (d, 3H) 2.98 (d, 3H) 3.64-3.80 (m, 1H) 4.35-4.57 (m, 2H) 6.76 (d, 1H) 7.00 (s, 1H) 7.69 (s, 1H) 7.75 (s, 1H). MS APCI, m/z=360 (M+H). HPLC Method B: 2.19 min.

The compounds of Examples 3 to 21 illustrated in Table 1 were synthesized in accord with the processes described herein by the use of suitable intermediates.

Example 3

5-[7-Chloro-2-((S)-1-cyclopropyl-ethyl)-1-oxo-2,3-dihydro-1H-isoindol-5-yl]-isoxazole-3-carboxylic acid amide Example 4

5-[2-((S)-1-Cyclopropyl-ethyl)-7-methyl-1-oxo-2,3-dihydro-1H-isoindol-5-yl]-isoxazole-3-carboxylic acid amide Example 5

5-(2-Isopropyl-7-methyl-1-oxo-2,3-dihydro-1H-isoindol-5-yl)-isoxazole-3-carboxylic acid dimethylamide

Example 6

5-[2-((S)-1-Cyclopropyl-ethyl)-7-methyl-1-oxo-2,3-dihydro-1H-isoindol-5-yl]-isoxazole-3-carboxylic acid methylamide

Example 7

5-[7-Chloro-2-((S)-1-cyclopropyl-ethyl)-1-oxo-2,3-dihydro-1H-isoindol-5-yl]-isoxazole-3-carboxylic acid amide

Example 8

5-[2-((S)-1-Cyclopropyl-ethyl)-7-methyl-1-oxo-2,3-dihydro-1H-isoindol-5-yl]-isoxazole-3-carboxylic acid dimethylamide

Example 9

7-Chloro-2-isopropyl-5-[3-(pyrrolidine-1-carbonyl)-isoxazol-5-yl]-2,3-dihydro-isoindol-1-one

Example 10

5-(7-Chloro-2-isopropyl-1-oxo-2,3-dihydro-1H-isoindol-5-yl)-isoxazole-3-carboxylic acid (2-hydroxy-ethyl)-methyl-amide

Example 11

5-[7-Methyl-1-oxo-2-((S)-2,2,2-trifluoro-1-methyl-ethyl)-2,3-dihydro-1H-isoindol-5-yl]-isoxazole-3-carboxylic acid dimethylamide

Example 12

5-[2-((S)-1-Cyclopropyl-ethyl)-7-methyl-1-oxo-2,3-dihydro-1H-isoindol-5-yl]-isoxazole-3-carboxylic acid isopropyl-methyl-amide

Example 13

5-[2-((S)-1-Cyclopropyl-ethyl)-7-methyl-1-oxo-2,3-dihydro-1H-isoindol-5-yl]-isoxazole-3-carboxylic acid (2-hydroxy-ethyl)-methyl-amide

Example 14

5-(7-Chloro-2-isopropyl-1-oxo-2,3-dihydro-1H-isoindol-5-yl)-isoxazole-3-carboxylic acid cyclopentylamide

Example 15

7-Chloro-2-isopropyl-5-[3-(morpholine-4-carbonyl)-isoxazol-5-yl]-2,3-dihydro-isoindol-1-one

Example 16

2-((S)-1-Cyclopropyl-ethyl)-7-methyl-5-[3-(piperazine-1-carbonyl)-isoxazol-5-yl]-2,3-dihydro-isoindol-1-one

Example 17

5-[7-Chloro-1-oxo-2-((S)-2,2,2-trifluoro-1-methyl-ethyl)-2,3-dihydro-1H-isoindol-5-yl]-isoxazole-3-carboxylic acid dimethylamide

Example 18

5-[7-Chloro-2-((S)-1-cyclopropyl-ethyl)-1-oxo-2,3-dihydro-1H-isoindol-5-yl]-isoxazole-3-carboxylic acid isopropyl-methyl-amide

Example 19

5-[7-Chloro-2-((S)-1-cyclopropyl-ethyl)-1-oxo-2,3-dihydro-1H-isoindol-5-yl]-isoxazole-3-carboxylic acid (2-hydroxy-ethyl)-methyl-amide

Example 20

7-Chloro-2-((S)-1-cyclopropyl-ethyl)-5-[3-(morpholine-4-carbonyl)-isoxazol-5-yl]-2,3-dihydro-isoindol-1-one

Example 21

7-Chloro-5-[3-(morpholine-4-carbonyl)-isoxazol-5-yl]-2-((S)-2,2,2-trifluoro-1-methyl-ethyl)-2,3-dihydro-isoindol-1-one

TABLE 1

| Example No. | Structure | MW | M + H | RT (HPLC) |
|---|---|---|---|---|
| 1 | 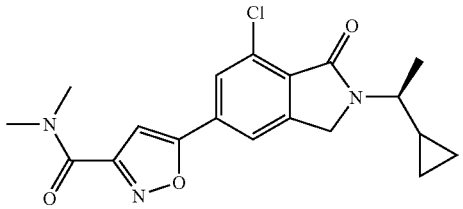 | 373.8 | 374.2 | 0.70 |

TABLE 1-continued

| Example No. | Structure | MW | M + H | RT (HPLC) |
|---|---|---|---|---|
| 2 | 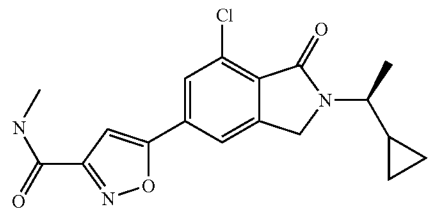 | 359.8 | 360.1 | 2.19 |
| 3 | 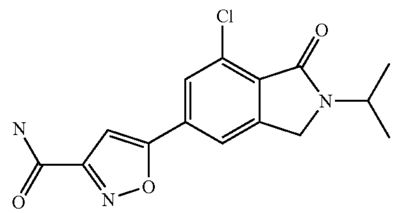 | 319.7 | 320.0 | 1.91 |
| 4 | 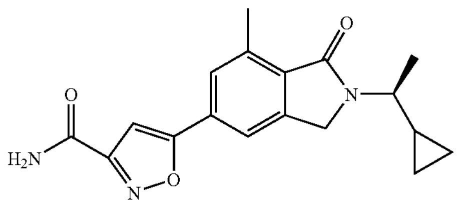 | 325.4 | 326.1 | 2.21 |
| 5 | 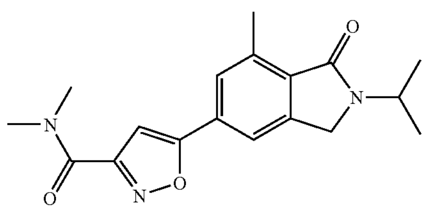 | 327.4 | 328.4 | 2.19 |
| 6 | 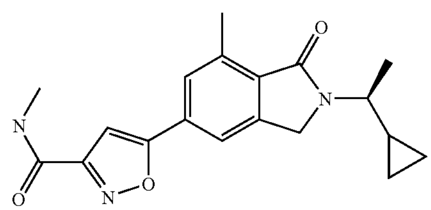 | 339.4 | 340.1 | 2.30 |
| 7 | 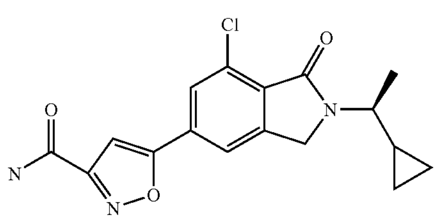 | 345.8 | 346.0 | 2.10 |
| 8 | 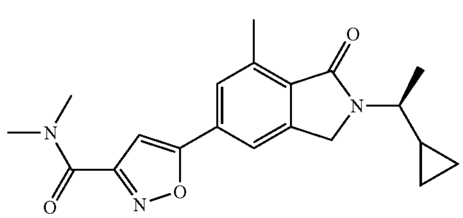 | 353.4 | 354.4 | 2.29 |

TABLE 1-continued

| Example No. | Structure | MW | M + H | RT (HPLC) |
|---|---|---|---|---|
| 9 | 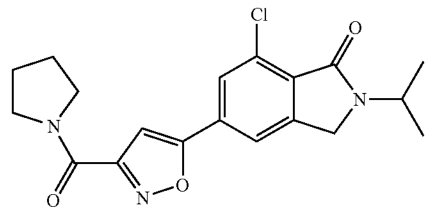 | 373.8 | 374.0 | 2.32 |
| 10 | 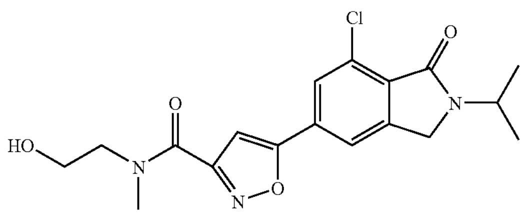 | 377.8 | 378.0 | 1.87 |
| 11 | 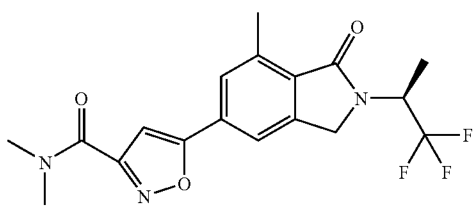 | 381.4 | 382.0 | 2.40 |
| 12 | 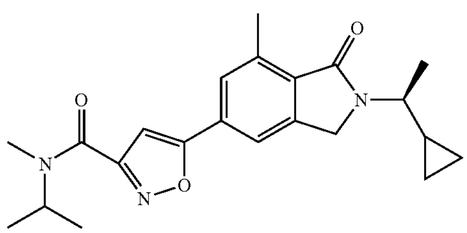 | 381.5 | 328.3 | 2.58 |
| 13 | 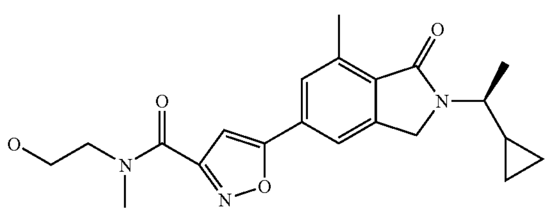 | 383.4 | 384.2 | 2.12 |
| 14 | 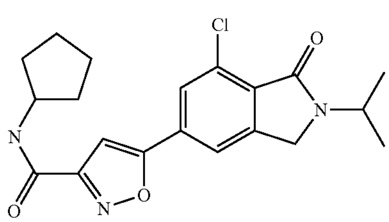 | 387.9 | 388.1 | 2.50 |
| 15 | 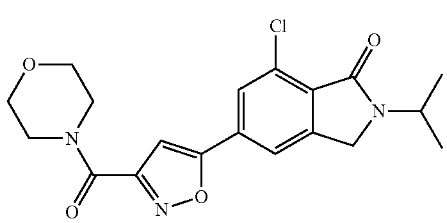 | 389.8 | 390.0 | 2.12 |

TABLE 1-continued
| Example No. | Structure | MW | M + H | RT (HPLC) |
|---|---|---|---|---|
| 16 | 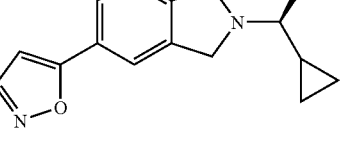 | 394.5 | 395.2 | 1.77 |
| 17 | 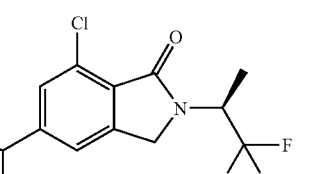 | 401.8 | 402.0 | 2.36 |
| 18 | 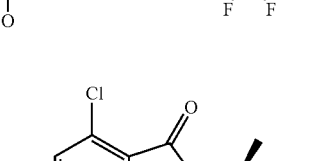 | 401.9 | 402.3 | 2.53 |
| 19 | 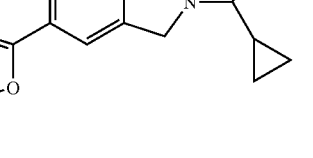 | 403.9 | 384.2 | 2.05 |
| 20 | 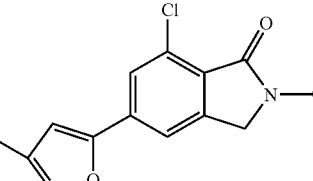 | 415.9 | 416.1 | 2.31 |
| 21 | 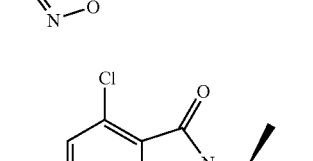 | 443.8 | 444.0 | 2.36 |
MW is calculated molecular weight
M + H is mass as measured
RT is retention time in HPLC in minutes. Method A was used for Example 1 and Method B for Examples 2 through 21 inclusive.

Pharmaceutical Compositions

The compounds described herein may be generally formulated into a pharmaceutical composition comprising a compound of Formula I or a pharmaceutically acceptable salt or solvate thereof, in association with a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substance, which may also act as diluents, flavoring agents, solubilizers, lubricants, suspending agents, binders or table disintegrating agents. A solid carrier can also be an encapsulating material.

In powders, the carrier is a finely divided solid, which is in a mixture with the finely divided compound active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be made as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, more particularly, from about 0.10% w to 50% w, of the compound of the invention, all percentages by weight being based on the total weight of the composition.

A therapeutically effective amount for the practice of the present invention can be determined by one of ordinary skill in the art using known criteria including the age, weight and response of the individual patient, and interpreted within the context of the disease that is being treated or being prevented.

Medical Uses

Compounds described herein exhibit activity as modulators of metabotropic glutamate receptors and more particularly exhibit activity as potentiators of the mGluR2 receptor. It is contemplated that the compounds will be useful in therapy as pharmaceuticals, in particular for the treatment of neurological and psychiatric disorders associated with glutamate dysfunction in an animal and particularly in a human.

More specifically, the neurological and psychiatric disorders include, but are not limited to, disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, and conduct disorder.

The invention thus provides a use of any of the compounds according to Formula I, or a pharmaceutically acceptable salt or solvate thereof, for the manufacture of a medicament for the treatment of any of the conditions discussed above.

Additionally, the invention provides a method for the treatment of a subject suffering from any of the conditions discussed above, whereby an effective amount of a compound according to Formula I or a pharmaceutically acceptable salt or solvate thereof, is administered to a patient in need of such treatment. The invention also provides a compound of Formula I or pharmaceutically acceptable salt or solvate thereof, as hereinbefore defined for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses the administration of an effective amount of a compound of the present invention, to mitigate either a pre-existing disease state, acute or chronic, or to mitigate a recurring condition. This definition also encompasses prophylactic therapies for prevention of recurring conditions and continued therapy for chronic disorders.

In use for therapy in a warm-blooded animal such as a human, the compounds of the present invention may be administered in the form of a conventional pharmaceutical composition by any route including orally, intramuscularly, subcutaneously, topically, intranasally, intraperitoneally, intrathoracically, intravenously, epidurally, intrathecally, intracerebroventricularly and by injection into the joints. In preferred embodiments of the invention, the route of administration is oral, intravenous, or intramuscular.

The dosage will depend on the route of administration, the severity of the disease, age and weight of the patient and other factors normally considered by the attending physician, who determines the individual regimen and dosage level for a particular patient.

As mentioned above, the compounds described herein may be provided or delivered in a form suitable for oral use, for example, in a tablet, lozenge, hard and soft capsule, aqueous solution, oily solution, emulsion, and suspension. Alternatively, the compounds may be formulated into a topical administration, for example, as a cream, ointment, gel, spray, or aqueous solution, oily solution, emulsion or suspension. The compounds described herein also may be provided in a form that is suitable for nasal administration, for example, as a nasal spray, nasal drops, or dry powder. The compounds can be administered to the vagina or rectum in the form of a suppository. The compounds described herein also may be administered parentally, for example, by intravenous, intravesicular, subcutaneous, or intramuscular injection or infusion. The compounds can be administered by insufflation (for example as a finely divided powder). The compounds may also be administered transdermally or sublingually.

In addition to their use in therapeutic medicine, the compounds of Formula I, or salts thereof, are useful as pharmacological tools in the development and standardization of in vitro and in vivo test systems for the evaluation of the effects of inhibitors of mGluR-related activity in laboratory animals as part of the search for new therapeutics agents. Such animals include, for example, cats, dogs, rabbits, monkeys, rats and mice.

A compound of Formula I or a pharmaceutically acceptable salt, solvate or in vivo hydrolysable ester thereof, or a pharmaceutical composition or formulation comprising a compound of Formula I may be administered concurrently, simultaneously, sequentially or separately with another pharmaceutically active compound or compounds selected from the following:

(i) antidepressants such as amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robalzotan, sertraline, sibutramine, thionisoxetine, tranylcypromaine, trazodone, trimipramine, venlafaxine and equivalents and pharmaceutically active isomer(s) and metabolite(s) thereof;

(ii) atypical antipsychotics including for example quetiapine and pharmaceutically active isomer(s) and metabolite(s) thereof;

(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof;

(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof;

(v) anticonvulsants including for example carbamazepine, valproate, lamotrogine, gabapentin and equivalents and pharmaceutically active isomer(s) and metabolite(s) thereof;

(vi) Alzheimer's therapies including for example donepezil, memantine, tacrine and equivalents and pharmaceutically active isomer(s) and metabolite(s) thereof;

(vii) Parkinson's therapies including for example deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof;

(viii) migraine therapies including for example almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof;

(ix) stroke therapies including for example abciximab, activase, NXY-059, citicoline, crobenetine, desmoteplase, repinotan, traxoprodil and equivalents and pharmaceutically active isomer(s) and metabolite(s) thereof;

(x) urinary incontinence therapies including for example darafenacin, falvoxate, oxybutynin, propiverine, robalzotan, solifenacin, tolterodine and equivalents and pharmaceutically active isomer(s) and metabolite(s) thereof;

(xi) neuropathic pain therapies including for example gabapentin, lidoderm, pregablin and equivalents and pharmaceutically active isomer(s) and metabolite(s) thereof;

(xii) nociceptive pain therapies such as celecoxib, etoricoxib, lumiracoxib, rofecoxib, valdecoxib, diclofenac, loxoprofen, naproxen, paracetamol and equivalents and pharmaceutically active isomer(s) and metabolite(s) thereof;

(xiii) insomnia therapies including for example allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos, secobarbital, zaleplon, zolpidem and equivalents and pharmaceutically active isomer(s) and metabolite(s) thereof, or (xiv) mood stabilizers including for example carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combination products employ the compound of this invention within the dosage range described herein and the other pharmaceutically active compound or compounds within approved dosage ranges and/or the dosage described in the publication reference.

Biological Assays

The pharmacological properties of the compounds of the invention can be analyzed using standard assays for functional activity. Examples of glutamate receptor assays are well known in the art as described in, for example, Aramori et al., 1992, Neuron, 8:757; Tanabe et al., 1992, Neuron, 8:169; Miller et al., 1995, J. Neuroscience, 15:6103; Balazs, et al., 1997, J. Neurochemistry, 1997, 69:151. The methodology described in these publications is incorporated herein by reference. Conveniently, the compounds of the invention can be studied by means of an assay that measures the mobilization of intracellular calcium, $[Ca^{2+}]_i$ in cells expressing mGluR2.

hERG activity was assessed using the process described by Bridgland-Taylor, M. H., et al, J. Pharm. Tox. Methods 54 (2006) 189-199.

Solubility was determined in pH 7.4 phosphate buffer after equilibration for 24 h at 25° C. and HPLC-UV and LC-MSMS were used for quantitation.

A [$^{35}$S]-GTPγS binding assay was used to functionally assay mGluR2 receptor activation. The allosteric activator activity of compounds at the human mGluR2 receptor were measured using a [$^{35}$S]-GTPγS binding assay with membranes prepared from CHO cells that stably express the human mGluR2. The assay is based upon the principle that agonists bind to G-protein coupled receptors to stimulate GDP-GTP exchange at the G-protein. Since [$^{35}$S]-GTPγS is a non-hydrolyzable GTP analog, it can be used to provide an index of GDP-GTP exchange and, thus, receptor activation. The GTPγS binding assay therefore provides a quantitative measure of receptor activation.

Membranes were prepared from CHO cells stably transfected with human mGluR2. Membranes (30 μg protein) were incubated with test compound (3 nM to 300 μM) for 15 minutes at room temperature prior to the addition of 1 μM glutamate, and incubated for 30 min at 30° C. in 500 μl assay buffer (20 mM HEPES, 100 mM NaCl, 10 mM MgCl$_2$), containing 30 μM GDP and 0.1 nM [$^{35}$S]-GTPγS (1250 Ci/mmol). Reactions were carried out in triplicate in 2 ml polypropylene 96-well plates. Reactions were terminated by vacuum filtration using a Packard 96-well harvester and Unifilter-96, GF/B filter microplates. The filter plates were washed 4×1.5 ml with ice-cold wash buffer (10 mM sodium phosphate buffer, pH 7.4). The filter plates were dried and 35 μl of scintillation fluid (Microscint 20) was added to each well. The amount of radioactivity bound was determined by counting plates on the Packard TopCount. Data was analyzed using GraphPad Prism, and $EC_{50}$ and $E_{max}$ values (relative to the maximum glutamate effect) were calculated using non-linear regression.

As illustrated in Table 2, below, generally, compounds described herein have favourable solubility, low capacity to activate the hERG ion channel and were highly active in assays described herein for mGluR2 modulator activity, having $EC_{50}$ values as shown.

TABLE 2

| Example No. | Hu GTPgS EC50 (nM) | Hu GTPgS Median Top Effect (%) | Solubility (μM) | hERG Mean IC50 (M) |
| --- | --- | --- | --- | --- |
| 1 | 64 | 127 | 33.4 | >3.30E−05 |
| 2 | 600 | 114 | 6.82 | 2.10E−05 |
| 3 | 214 | 117 | 21.4 | >3.30E−05 |
| 4 | 150 | 130 | 9.53 | >3.30E−05 |
| 5 | 425 | 67 | 19.2 | >3.30E−05 |
| 6 | 510 | 110 | 17.5 | 2.30E−05 |
| 7 | 230 | 139 | 16.6 | >3.30E−05 |
| 8 | 115 | 123 | 31.1 | >3.30E−05 |
| 9 | 37 | 101 | 3.57 | >3.30E−05 |
| 10 | 618 | 103 | 54.1 | >3.30E−05 |
| 11 | 66 | 114 | 4.35 | >3.30E−05 |
| 12 | 36 | 100 | 11.2 | >3.30E−05 |
| 13 | 479 | 78 | 153 | >3.30E−05 |
| 14 | 60 | 97 | 3.53 | 1.90E−05 |
| 15 | 530 | 100 | 66.3 | >3.30E−05 |
| 16 | 664 | 79 | 435 | >3.30E−05 |
| 17 | 84 | 139 | 15.5 | >3.30E−05 |
| 18 | 56 | 109 | 4.65 | >3.30E−05 |
| 19 | 443 | 141 | 273 | >3.30E−05 |
| 20 | 85 | 122 | 5.74 | >3.30E−05 |
| 21 | 514 | 106 | 9.32 | >3.30E−05 |

The invention claimed is:

1. A compound that is 7-Chloro-2-isopropyl-5-[3-(morpholine-4-carbonyl)-isoxazol-5-yl]-2,3-dihydro-isoindol-1-one or a pharmaceutically acceptable salt thereof.

2. A compound according to claim 1 in the form of a pharmaceutically acceptable salt.

3. A compound according to claim 2 wherein the pharmaceutically acceptable salt is a hydrochloride, a hydrobromide, a phosphate, an acetate, a fumarate, a maleate, a tartrate, a citrate, a methanesulphonate or a p-toluenesulphonate.

4. A method of making a compound according to claim 1, comprising:
   converting a 4-bromo-aniline to a corresponding nitrile under Sandmeyer reaction conditions;
   converting the nitrile to an amide by hydrolysing with a base;
   diazotizing the amide and then hydrolysing with nitrososulphuric acid to provide a benzoic acid;
   protecting the benzoic acid as a methyl ester;
   monobrominating the benzylic methyl group with N-bromosuccinimide using benzoyl peroxide as the radical initiator to yield 6-substituted 4-bromo-2-bromomethyl-benzoic acid methyl ester;
   cyclizing the 6-substituted 4-bromo-2-bromomethyl-benzoic acid methyl ester to an 4-bromo isoindoline with an amine;
   reacting the 4-bromo-isoindolone under Sonagashira conditions with a protected acetylene;
   deprotecting the acetylene with a base;
   reacting the deprotected acetylene with ethyl 2-chloro-2-(hydroxyimino)acetate to generate an isoxazole ester, and
   hydrolysing the ester to the acid and amidating using isobutylchloroformate and N-methyl morpholine and an appropriate amine to generate a compound of claim 1, or,
   generating a compound of claim 1 from an isoxazole ester by reaction with an amine and heating.

5. A pharmaceutical composition comprising a compound or a pharmaceutically acceptable salt thereof according to claim 1 and at least one pharmaceutically acceptable carrier or excipient.

6. A method of alleviating symptoms or slowing the appearance of symptoms of schizophrenia or anxiety in a subject in need thereof, comprising the step of administering to said subject a therapeutically effective amount of a compound or a pharmaceutically acceptable salt thereof according to claim 1.

7. A method of alleviating symptoms or slowing the appearance of symptoms of schizophrenia or anxiety in a subject in need thereof, comprising the step of administering to said subject a therapeutically effective amount of a pharmaceutical composition according to claim 5.

* * * * *